United States Patent [19]

Attig et al.

[11] Patent Number: 4,560,672

[45] Date of Patent: Dec. 24, 1985

[54] RUTHENIUM-COPPER-CONTAINING, ACTIVATED-CARBON-SUPPORTED CATALYST AND PROCESS FOR MAKING ALCOHOL USING SAME

[75] Inventors: Thomas G. Attig, Aurora; Anne M. Graham, Northfield Center; Frederick Pesa, Aurora, all of Ohio

[73] Assignee: The Standard Oil Company, Cleveland, Ohio

[21] Appl. No.: 616,968

[22] Filed: Jun. 4, 1984

[51] Int. Cl.$^4$ .................. B01J 23/02; B01J 23/40; B01J 27/24; B01J 23/06
[52] U.S. Cl. .................. 502/183; 502/184; 502/185; 502/200; 502/340; 502/345; 518/713; 518/726
[58] Field of Search .............. 502/183, 184, 185, 200, 502/340, 345

[56] References Cited

U.S. PATENT DOCUMENTS

| | | | |
|---|---|---|---|
| 3,193,584 | 7/1965 | Rylander et al. | 502/185 |
| 3,901,664 | 8/1975 | Kozlowski et al. | 44/56 |
| 4,077,912 | 3/1978 | Dolhyj et al. | 252/461 |
| 4,298,354 | 11/1981 | Hardman et al. | 44/56 |
| 4,377,643 | 3/1983 | Pesa et al. | 502/178 X |
| 4,478,955 | 10/1984 | Pesa et al. | 518/713 |

FOREIGN PATENT DOCUMENTS 49-3757 7/1970 Japan .................. 502/185

OTHER PUBLICATIONS

Calgon Corporation Product Literature Entitled "Type PCB Granular Carbon".
Calgon Corporation Product Literature Entitled "Type BPL Granular Carbon".

Primary Examiner—John Doll
Assistant Examiner—William G. Wright
Attorney, Agent, or Firm—Larry Evans; Joseph Curatolo

[57] ABSTRACT

A catalyst is disclosed which comprises a ruthenium-copper-containing complex of the formula $$M_aA_bRuCu_cN_zO_x$$

wherein
 M is selected from the group consisting of Ce, Cr, Fe, Mn, and mixtures thereof,
 A is an alkali metal, alkaline earth metal or mixture thereof,
 a is from 0 to about 1,
 b is from about 0.002 to about 10,
 c is from about 0.2 to about 20,
 z is from 0 to about 1% by weight,
 x is the number of oxygens needed to fulfill the valence requirements of the other elements, said complex being supported by an activated carbon support having a surface area of at least about 300 square meters per gram. A process for converting mixtures of hydrogen and carbon monoxide, particularly synthesis gas, to alcohol with minimal levels of hydrocarbon by-products being formed is also disclosed.

10 Claims, No Drawings

RUTHENIUM-COPPER-CONTAINING, ACTIVATED-CARBON-SUPPORTED CATALYST AND PROCESS FOR MAKING ALCOHOL USING SAME

TECHNICAL FIELD

This invention relates to catalysts and to processes for making alcohol using such catalysts. More particularly, this invention relates to a ruthenium-cooper-containing, activated-carbon supported catalytic complex which is useful in converting gaseous mixtures of hydrogen and carbon monoxide, particularly synthesis gas, to alcohol with minimal levels of hydrocarbon by-products.

BACKGROUND OF THE INVENTION

Synthesis gas may be defined as any of several gaseous mixtures used for synthesizing a wide range of compounds, both organic and inorganic. Such mixtures result from reacting carbon-rich substances with steam (steam reforming) or steam and oxygen (partial oxidation). These mixtures contain chiefly carbon monoxide and hydrogen, and usually low percentages of carbon dioxide and nitrogen (less than 2%). The organic source materials may be natural gas, methane, naphtha, heavy petroleum oils or coke. The reactions are usually nickel-catalyzed steam-cracking (reforming) of methane or natural gas ($CH_4 + H_2O \rightarrow CO + 3H_2$); partial oxidation of methane, naphtha, or heavy oils; and (especially in view of the petroleum shortage) the water-gas reaction with coke ($C + H_2O \rightarrow CO + H_2$).

It is known to use transition-metal catalysts to convert synthesis gas to alcohols, aldehydes, acrylic acid, etc. A continuing problem exists, however, in finding suitable catalysts for selectively converting synthesis gas to alcohol with only minimal levels of hydrocarbon by-products.

U.S. Pat. No. 4,298,354 discloses an oxidecomplex catalyst containing copper, thorium, an alkali metal and at least one other metal selected from the group consisting of Ca, Mo, Rh, Mn, Pt, Ce, Cr, Zn, Al, Ti, La, V, U, Ru, Re, and Pd. These catalysts are useful in converting synthesis gas to alcohols, such alcohols containing from 2 to 6 carbon atoms and normally not more than 85% methanol by weight.

U.S. Pat. No. 4,377,643 discloses the production of alkanes and oxygenated hydrocarbons, particularly alcohols, from synthesis gas using a catalytic complex containing ruthenium, copper, an alkali metal and a promoter selected from the group consisting of Rh, Ir, Pd, and Pt.

It would be advantageous to provide a catalytic complex for converting mixtures of hydrogen and carbon monoxide, particularly synthesis gas, to alcohol with only minimal levels of hydrocarbon by-products.

SUMMARY OF THE INVENTION

The present invention contemplates the provision of a ruthenium-copper containing catalytic complex supported by an activated carbon support that is particularly suitable for converting gaseous mixtures of hydrogen and carbon monoxide, particularly synthesis gas, to alcohol with only minimal levels of hydrocarbon by-products.

Broadly stated, the present invention provides for a catalyst comprising a ruthenium-copper-containing complex of the formula $$M_a A_b RuCu_c N_z O_x$$

wherein
M is selected from the group consisting of Ce, Cr, Fe, Mn, and mixtures thereof,
A is an alkali metal, alkaline earth metal or a mixture thereof,
a is from 0 to about 1,
b is from about 0.002 to about 10,
c is from about 0.2 to about 20,
z is from 0 to about 1% by weight, x is the number of oxygens needed to fulfill the valence requirements of the other elements, said complex being supported by
an activated carbon support having a surface area of at least about 300 square meters per gram.

The present invention further provides for a process for producing alcohol comprising contacting a gaseous reactant containing carbon monoxide and hydrogen with a catalyst comprising
a ruthenium-copper-containing complex of the formula $$M_a A_b RuCu_c N_z O_x$$

wherein
M is selected from the group consisting of Ce, Cr, Fe, Mn, and mixtures thereof,
A is an alkali metal, alkaline earth metal or mixture thereof,
a is from 0 to about 1,
b is from about 0.002 to about 10,
c is from about 0.2 to about 20,
z is from 0 to about 1% by weight,
x is the number of oxygens needed to fulfill the valence requirements of the other elements, said complex being supported by
an activated carbon support having a surface area of at least about 300 square meters per gram.

DESCRIPTION OF THE PREFERRED EMBODIMENTS

Catalyst

The novel catalysts provided in accordance with the present invention are constituted of a ruthenium-copper-containing catalytic complex of the formula $$M_a A_b RuCu_c N_z O_x$$

wherein
M is selected from the group consisting of Ce, Cr, Fe, Mn, and mixtures thereof;
A is an alkali metal, alkaline earth metal or mixture thereof;
a is from 0 to about 1, preferably from about 0.1 to about 0.5;
b is from about 0.002 to about 10, preferably from about 0.02 to about 6;
c is from about 0.2 to about 20, preferably from about 0.4 to about 10;
z is from 0 to about 1%, preferably from about 0.5% to about 1% by weight;
x is the number of oxygens needed to fulfill the valence requirements of the other elements, said complex being supported by an activated carbon support having a surface area of at least about 300 square meters per gram, preferably about 300 to about 2500 square meters per gram, more preferably about 1050 to about 1250 square meters per gram.

The weight ratio of the ruthenium-copper-containing complex to the activated carbon support is in the range of about 30:70 to about 1:99, preferably about 10:90 to about 3:97, and advantageously about 5:95.

A can be selected from the group consisting of Na, Li, K, Rb, Cs, Be, Mg, Ca, Sr, Ba and mixtures thereof. A is preferably Na, Li, K, Rb, Cs, Mg or mixtures thereof.

A critical feature of the catalysts of the invention is the activated carbon support. The employment of such support is critical due to the fact that the process of the invention achieves a significantly high degree of selectivity to alcohols because of the use of such support. This result was unexpected. Without the activated carbon support, the high degree of selectively to alcohols with the inventive process cannot be achieved.

The term "activated carbon" is used herein to refer to an amorphous form of carbon characterized by high adsorptivity for many gases, vapors and colloidal solids. The sources of activated carbon and the techniques for preparing it are well known to those skilled in the art and, accordingly, need not be described in detail herein. Briefly, activated carbon is usually obtained by the destructive distillation of wood, nut shells, animal bones or other carbonaceous material. It is typically "activated" by heating to about 800°–900° C. with steam or carbon dioxide which results in a porous internal structure (honeycomb-like).

The activated carbon supports of the present invention are characterized by a high surface area being, as indicated above, at least about 300 square meters per gram, perferably about 300 to about 2500 square meters per gram. These supports may consist entirely of activated carbon or may have an inert core coated with a layer of activated carbon. The inert core materials that are suitable for use are entirely conventional and include, for example, silica, Alundum, clay, alumina-silica, silicon carbide and alumina. An example of such a coated support is activated charcoal coated on an Alundum core. The preparation of such activated carbon supports, both those consisting entirely of activated carbon and those containing an inert core, are entirely conventional and, accordingly, need not be described herein.

Typical physical properties for the activated carbon supports of the invention are:

Surface Area: 1050–1250 m$^2$/g.
Bulk Density, dense packing: 0.44–0.48 g/cc.
Particle Density (Hg Displacement): 0.85 g/cc.
Real Density (He Displacement): 2.1–2.2 g/cc.
Pore Volume (Within Particle): 0.7–0.72 cc/g.
Voids in Dense Packed Column: 43–50%
Specific Heat at 100° C.: 0.25

Typical mesh sizes (U.S. Sieve Series) include $4 \times 10$, $6 \times 16$ and $12 \times 30$, the preferred size being dependent on the specific application. Examples of commercially available activated carbon supports that are suitable for use in accordance with the present invention include the activated carbons sold by Calgon Corporation under the designations "Type BPL" and "Type PCB".

The catalytic complex of the present invention is a mixed-metal oxide. In the process of the invention, the catalyst is preferably utilized in a partially reduced state. However, the catalyst is generally not totally reduced to elemental metal and thus retains an oxide character.

The catalysts of the invention may be prepared by conventional procedures known to those skilled in the art. Typically these procedures involve first mixing compounds containing the catalytic components in a liquid solution or slurry, (e.g., a water solution or slurry), and thereafter coating or impregnating the activated carbon support with such components. Suitable compounds containing the catalytic components include but are not limited to oxides, hydroxides, inorganic salts (e.g., nitrates, phosphates, halides, carbonates, silicates, aluminates) and salts of organic acids (e.g., acetates, formates, butyrates, propionates, benzylates and the like).

Coating techniques usually involve the steps of first precipitating the catalytic components from the solution of slurry. The precipitate can be formed by initially forming an aqueous solution of the ruthenium, copper and "M" metal (if any) components, adding an alkali or alkaline earth metal hydroxide to such solution to precipitate the catalytic components, heating the mixture in the presence of the alkali or alkaline earth, metal, and thereafter filtering the precipitate. The precipitate can then be dried and, optionally, calcined, and/or ground to a desired particle size.

A particularly useful coating procedure is disclosed in U.S. Pat. No. 4,077,912, which is incorporated herein by reference. Breifly, this method involves partially wetting the activated carbon support, contacting the partially wetted support with a powdered precipitate of the catalytic components, then gently agitating the mixture until the catalytic complex is formed.

Agitation is conveniently conducted by placing the partially wetted support in a rotating drum and adding the powdered precipitate until none is taken up by the support. The liquid used to wet the support may include inorganic or organic liquids and is dependent upon the type of catalytic components employed. The liquid and the catalytic components should have a relatively high degree of attraction for each other.

The catalytic components can also be impregnated on the active carbon support by depositing a solution containing the catalytic components on the carrier using known techniques, then drying and calcining.

The catalytic components may optionally be individually coated or impregnated on the active carbon-containing support using the above-indicated techniques.

After the catalytic components are coated or impregnated on the active carbon support, the resulting catalytic complex is partially reduced and, optionally, nitrided. Partial reduction can be effected using known techniques. A preferred technique involves packing the catalyst into a stainless steel tube which is then placed in an oven. Hydrogen is introduced into the oven at atmospheric pressure at about 150–200 cc/min. The temperature is initially set at 100° C., then increased by 50° C. over a 15-minute period, then maintained at that temperature for an additional 15 minutes; this procedure is continued until a temperature of 500° C. is reached. The temperature is maintained at 500° C. for two hours, the catalyst is then cooled to room temperature under a flow of hydrogen. For the catalytic complexes that are nitrided, ammonia is substituted for hydrogen and the oven is set at 400° C. After three hours at 400° C., the catalyst is cooled under ammonia, and the tube is capped until the catalyst is needed for use. Optionally, the catalyst can be reduced at only 350° C., the same procedure being used as indicated above, with the exception that when a temperature of 350° C. is reached, the temperature of catalyst is then maintained at 350° C. for two hours, then cooled to room temperature.

PROCESS

The inventive process is carried out by contacting the gaseous reactant with the above-described catalytic complex in a suitable reactor. The reaction can be carried out in either a fluid-bed mode or fixed-bed mode, continuously or in batch operation.

Although synthesis gas is a preferred reactant, any other gas composed primarily of hydrogen and carbon monoxide and having an $H_2/CO$ mole ratio of about 1:10 to 10:1, preferably about 1:3 to 3:1 can be employed. The gaseous reactant should contain as little sulfur as possible since sulfur is a known poison for copper containing catalysts. Preferably the gaseous reactant is essentially sulfur-free.

The space velocity of the gaseous reactant is not critical but should be about 100 to about 10,000, preferably about 500 to about 5000 liters of gaseous reactant per liter of catalyst per hour.

The reaction pressure should normally be from about 500 to about 5000 psi and is preferably from about 500 to about 2000 psi. Although there is no real upper limit to the reaction pressure, pressures higher than 2000 psi are normally not employed because of the high expense involved. Also, pressures as low as 250 psi can be employed, although it is preferably to operate at at least about 500 psi because the formation of alcohols is favored at higher pressures.

The reaction temperature should be maintained between about 250°–400° C., preferably 250°–350° C. The reaction temperature, like the reaction pressure, is not critical, although a marked decrease in conversion rates will be obtained if temperatures and pressures lower than 500 psi and 250° C. are employed.

The contact time of the gaseous reactant with the catalyst is generally between about 10 seconds and about 200 seconds, preferably between about 15 seconds and about 140 seconds.

Product

The product produced by the process of the invention constitutes predominately a mixture of alcohols containing predominately methanol as well as significant amounts of higher alcohols usually having 2 to 8 carbon atoms. One of the advantages of the inventive process is that the formation of hydrocarbon by-products is relatively low, for example, below about 40% by weight, preferably below about 30% by weight and advantageously below about 15% by weight of the total weight of the products formed.

The alcohol mixtures formed in accordance with the inventive process are useful, for example, in expanding gasoline. The alcohol mixtures can be mixed with gasoline in any amount, and when present in amounts of less than 25%, no significant effect on the operation of an internal combustion engine containing the resulting gasoline/alcohol mixture will be noticed. Furthermore, the mixed alcohol products of the present invention can be mixed with any type of gasoline be it substantially all paraffinic such as alkylate or highly aromatic. Moreover, if the product alcohol mixture employed has no more than about 85% methanol, the resultant gasoline will be able to tolerate significant amounts of water without phase separation.

In order to further illustrate the catalytic complex and process of the present invention, the following examples are provided. Unless otherwise indicated, all parts and percentages are by weight.

EXAMPLE 1

A 25 cc. sample of 10-35 mesh activated carbon (Type BPL granular carbon purchased from Calgon Corporation) was evacuated and heated for 30 minutes at 45° C. in a rotary evaporator. A 15 ml. solution was made by dissolving 0.90 g. of copper nitrate and 0.63 g. sodium nitrate in 7.54 ml. of 10% aqueous ruthenium nitrate solution and diluting to 15 ml. total volume. This solution was added dropwise to the activated carbon while rotating under vacuum. When dried, the sample was removed, heated in flowing $H_2$ at 80° for one hour, maintained at 120° C. overnight, then maintained at 150° C. for three hours. The catalyst was reduced in flowing $H_2$ (200 cc/min.). During reduction, the temperature was increased 50° C. over a 15-minute period, then maintained at that temperature for 15 minutes before the next 50° C. increase. This procedure was repeated until a temperature of 500° C. was reached. The temperature was maintained at 500° C. for two hours. The catalyst was cooled to room temperature under flowing $H_2$ at 200 cc/min.

EXAMPLE 2

A previously dried (125° C. for three hours) 25 cc. sample of 10-30 mesh activated carbon (Type BPL granular carbon purchased from Calgon Corporation) was impregnated with a solution made by dissolving 1.81 g. of copper nitrate and 0.63 g. sodium nitrate in 7.54 g. of a 10.06% aqueous ruthenium nitrate solution. The sample was dried overnight at 110° C., then heated in flowing $N_2$ for two hours at 350° C. The catalyst was reduced to 500° C. using the procedure described in Example 1.

EXAMPLE 3

A 25 cc. sample of 10-30 mesh activated carbon (purchased from Alfa Corporation) was impregnated with the solution of copper nitrate, sodium nitrate and ruthenium nitrate described in Example 2. The sample was dried overnight at 110° C., then heated to 350° C. for three hours in air. The catalyst was reduced to 500° C. using the procedure described in Example 1, then nitrided in flowing $NH_3$ at 400° C. for three hours.

EXAMPLE 4

A 25 cc. sample of 10-30 mesh activated carbon (Type BPL granular carbon purchased from Calgon Corporation) was impregnated with the copper nitrate, sodium nitrate and ruthenium nitrate solution described in Example 2. The sample was dried overnight at 110° C.

The temperature was increased by 40° C. over a 15-minute interval, then maintained at that temperature for 15 minutes; the procedure being repeated until 350° C. was reached. The temperature was maintained at 350° C. for two hours in flowing nitrogen. The catalyst was reduced and nitrided using the procedure described in Example 3.

The process of the present invention is demonstrated by the following examples. A 20 cc. reactor was charged to the indicated pressure with hydrogen. A split block electric furnace which surrounded the reactor was activated and set for the run temperature. The system was allowed to equilibrate for at least 15 minutes at the run temperature before carbon monoxide flow was started and both gases were adjusted to the desired flow rates. The CO:H$_2$ mole ratio for each run was 3:7. After about one to one and one-half hours of reaction, the off-gas (effluent) was sampled and analyzed and the condensible product diverted from a pre-run receiver to a product collection receiver. A recovery run proceeded for one to three hours during which time the off-gas was analyzed by gas chromatography and its volume measured. The liquid produced was weighed and analyzed.

In addition to gas chromatography analysis for the gas phase, hydrocarbons having greater than three carbon atoms were determined by flame ionization detection. Liquid phase hydrocarbons and oxygenated hydrocarbons were analyzed by gas chromatography. The results reported in the Table below were calculated as follows.

CO conversion =

$$\frac{(\text{Moles of CO input} - \text{moles CO effluent}) \times 100}{\text{Moles of CO input}}$$

$$\text{Weight \%} = \frac{\text{Weight product identified} \times 100}{\text{Total product weight}}$$

Carbon dioxide and water were not considered in the calculations.

TABLE

| Run | Catalyst | Temp °C. | Pressure (PSIG) | Space Velocity (Hr$^{-1}$) | % CO Conv | Hydrocarbons | Alcohols | Other Oxygenated Compounds | Higher* Alcohols |
|---|---|---|---|---|---|---|---|---|---|
| 1 | Example 1 | 280 | 1300 | 3300 | 16.6 | 33.1 | 63.2 | 3.7 | 33.6 |
| 2 | Example 1 | 305 | 1300 | 3300 | 15.9 | 22.1 | 73.0 | 4.9 | 29.1 |
| 3 | Example 1 | 315 | 1300 | 3300 | 8.2 | 23.4 | 71.2 | 5.4 | 35.6 |
| 4 | Example 2 | 315 | 1300 | 3300 | 14.0 | 8.8 | 86.8 | 4.5 | 13.6 |
| 5 | Example 2 | 315 | 1300 | 3300 | 13.5 | 9.4 | 86.4 | 4.2 | 13.7 |
| 6 | Example 2 | 315 | 1300 | 3300 | 7.9 | 9.8 | 88.9 | 1.3 | 11.9 |
| 7 | Example 2 | 315 | 1000 | 5500 | 2.3 | 7.2 | 91.7 | 1.0 | 11.1 |
| 8 | Example 2 | 315 | 1300 | 3300 | 11.1 | 12.1 | 87.2 | 0.8 | 10.0 |
| 9 | Example 2 | 310 | 1000 | 2000 | 9.9 | 15.1 | 84.3 | 0.6 | 12.5 |
| 10 | Example 2 | 345 | 1300 | 3300 | 16.8 | 12.1 | 87.3 | 0.7 | 8.7 |
| 11 | Example 2 | 350 | 1300 | 3300 | 4.1 | 35.2 | 64.5 | 0.3 | 10.4 |
| 12 | Example 3 | 350 | 1300 | 3300 | 4.4 | 18.3 | 80.4 | 1.3 | 7.0 |
| 13 | Example 4 | 315 | 1300 | 3300 | 7.7 | 7.5 | 91.5 | 1.0 | 12.6 |
| 14 | Example 4 | 350 | 1300 | 3300 | 2.5 | 24.6 | 74.5 | 0.8 | 7.7 |
| 15 | Example 4 | 350 | 1300 | 3300 | 8.1 | 20.8 | 77.1 | 2.2 | 10.3 |
| 16 | Example 4 | 335 | 1300 | 3300 | 5.5 | 22.4 | 75.8 | 1.8 | 7.5 |

*C$_2$+ alcohols based on weight percent of total alcohols.

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:

1. A catalyst comprising a ruthenium-copper-containing complex of the formula $$M_aA_bRuCu_cN_zO_x$$

wherein
M is selected from the group consisting of Ce, Cr, Fe, Mn, and mixtures thereof,
A is an alkali metal, alkaline earth metal or mixture thereof,
a is from 0 to about 1,
b is from about 0.002 to about 10,
c is from about 0.2 to about 20,
z is from 0 to about 1% by weight,
x is the number of oxygens needed to fulfill the valence requirements of the other elements, said complex being supported by
an activated carbon support having a surface area of at least about 300 square meters per gram.

2. The catalyst of claim 1 wherein said support comprises an inert material coated with activated carbon.

3. The catalyst of claim 2 wherein said inert material is selected from the group consisting of silica, Alundum, clay, alumina-silica, silicon carbide and alumina.

4. The catalyst of claim 1 wherein said support has a surface area in the range of about 300 to about 2500 square meters per gram.

5. The catalyst of claim 1 wherein A is selected from the group consisting of Na, Li, K, Rb, Cs, Mg, or mixtures thereof.

6. The catalyst of claim 1 wherein a is about 0.1 to about 0.5.

7. The catalyst of claim 1 wherein b is about 0.02 to about 6.

8. The catalyst of claim 1 wherein c is from about 0.4 to about 10.

9. The catalyst of claim 1 wherein said catalyst is partially reduced.

10. The catalyst of claim 1 wherein the weight ratio of the ruthenium-copper-containing complex to the activated carbon support is about 30:70 to about 1:99.

* * * * *